(12) United States Patent
Pheiffer et al.

(10) Patent No.: US 11,382,603 B2
(45) Date of Patent: Jul. 12, 2022

(54) SYSTEM AND METHODS FOR PERFORMING BIOMECHANICALLY DRIVEN IMAGE REGISTRATION USING ULTRASOUND ELASTOGRAPHY

(71) Applicant: Siemens Healthcare GmbH, Erlangen (DE)

(72) Inventors: Thomas Pheiffer, Langhorne, PA (US); Ankur Kapoor, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 348 days.

(21) Appl. No.: 15/972,324

(22) Filed: May 7, 2018

(65) Prior Publication Data
US 2019/0336109 A1    Nov. 7, 2019

(51) Int. Cl.
*A61B 8/08*    (2006.01)
*A61B 8/13*    (2006.01)
(Continued)

(52) U.S. Cl.
CPC .............. *A61B 8/5246* (2013.01); *A61B 8/08* (2013.01); *A61B 8/13* (2013.01); *A61B 8/4245* (2013.01);
(Continued)

(58) Field of Classification Search
CPC ...... A61B 2034/2063; A61B 2090/364; A61B 5/4244; A61B 5/4381; A61B 6/032;
(Continued)

(56) References Cited

U.S. PATENT DOCUMENTS 6,775,404 B1    8/2004 Pagoulatos et al.
7,916,919 B2    3/2011 Zheng et al.
(Continued)

FOREIGN PATENT DOCUMENTS

WO    20180015414 A1    1/2018

OTHER PUBLICATIONS

Khallaghi, S. et al., "Statistical Biomechanical Surface Registration: Application to MR-TRUS Fusion for Prostate Interventions," IEEE Trans. Med. Imaging, vol. 34, No. 12, pp. 2535-2549, Dec. 2015.
(Continued)

*Primary Examiner* — Michael T Rozanski (57) ABSTRACT

A method and system for registering a pre-operative 3D medical image volume of a target organ to intra-operative ultrasound images is disclosed. An intra-operative 3D B-mode ultrasound volume and an intra-operative 3D ultrasound elastography volume are acquired. Patient-specific boundary conditions for a biomechanical tissue model of a target organ are determined using the intra-operative 3D B-mode volume. Patient-specific material properties for the biomechanical tissue model of the target organ are determined using the 3D ultrasound elastography volume. The target organ in the pre-operative 3D medical image volume is deformed using the biomechanical tissue model with the patient-specific material properties with the deformation of the target organ in the pre-operative 3D medical image volume constrained by the patient-specific boundary conditions.

19 Claims, 5 Drawing Sheets

(51) Int. Cl.
*A61B 8/00* (2006.01)
*G06T 7/00* (2017.01)
*G06T 15/08* (2011.01)
*G06T 7/33* (2017.01)
*G06T 7/37* (2017.01)
*A61B 5/055* (2006.01)
*A61B 6/03* (2006.01)
*A61B 5/00* (2006.01)
*A61B 90/00* (2016.01)

(52) U.S. Cl.
CPC .......... *A61B 8/485* (2013.01); *A61B 8/5261* (2013.01); *G06T 7/0012* (2013.01); *G06T 7/344* (2017.01); *G06T 7/37* (2017.01); *G06T 15/08* (2013.01); *A61B 5/055* (2013.01); *A61B 5/4244* (2013.01); *A61B 5/4381* (2013.01); *A61B 6/032* (2013.01); *A61B 2090/364* (2016.02); *G06T 2207/10081* (2013.01); *G06T 2207/10088* (2013.01); *G06T 2207/10136* (2013.01); *G06T 2207/30056* (2013.01); *G06T 2207/30081* (2013.01)

(58) Field of Classification Search
CPC .......... A61B 8/08; A61B 8/13; A61B 8/4245; A61B 8/485; A61B 8/5246; A61B 8/5261; G01S 15/8993; G01S 7/52042; G06T 15/08; G06T 19/20; G06T 2207/10081; G06T 2207/10088; G06T 2207/10132; G06T 2207/10136; G06T 2207/30056; G06T 2207/30081; G06T 2210/41; G06T 2219/2021; G06T 7/0012; G06T 7/33; G06T 7/344; G06T 7/37
See application file for complete search history.

(56) References Cited

U.S. PATENT DOCUMENTS

| | | | |
|---|---|---|---|
| 9,098,904 B2 | 8/2015 | Ji et al. | |
| 9,282,933 B2 | 3/2016 | Kiraly | |
| 9,375,195 B2 | 6/2016 | Kamen et al. | |
| 9,521,994 B2 | 12/2016 | Kamen et al. | |
| 2004/0234113 A1* | 11/2004 | Miga | G06T 7/0012 382/128 |
| 2013/0324841 A1 | 12/2013 | Kamen et al. | |
| 2016/0058424 A1 | 3/2016 | Fialkov | |
| 2016/0242745 A1 | 8/2016 | Yang et al. | |
| 2019/0200965 A1* | 7/2019 | Couade | A61B 8/06 |

OTHER PUBLICATIONS

Nir, G., et al., "Model-based registration of ex vivo and in vivo MRI of the prostate using elastography" IEEE Trans. Med. Imaging, vol. 32, No. 7, pp. 1349-1361, Jul. 2013.

* cited by examiner

SYSTEM AND METHODS FOR PERFORMING BIOMECHANICALLY DRIVEN IMAGE REGISTRATION USING ULTRASOUND ELASTOGRAPHY

BACKGROUND OF THE INVENTION

The present invention relates to registration of pre-operative volumetric medical images to intra-operative ultrasound images, and more particularly, to registering pre-operative volumetric medical images and intra-operative ultrasound images using a biomechanically driven image registration based on both B-mode ultrasound and ultrasound elastography.

Ultrasound is used to guide minimally invasive surgical procedures. For example, ultrasound can be used to guide interventions such as prostate needle biopsies and staging for liver lesion resection. In many ultrasound guided interventions, information provided by ultrasound can be enhanced by fusing the ultrasound with high resolution pre-operative medical images, such as computed tomography (CT) or magnetic resonance (MR). For example, ultrasound guided prostate needle biopsies can be improved by intra-operative registration with MR findings of suspected cancer nodules. Similarly, ultrasound guided staging for liver lesion resection can be improved by fusion with pre-operative CT images.

In order for pre-operative CT or MR to be effectively used to supplement ultrasound guidance, a quantitative registration transformation must be computed to fuse the images into a common coordinate space. In clinical practice, the images are often merely aligned mentally by the clinician after consulting both images visually. This can lead to inaccuracies and high inter-user and intra-user variability. Accordingly, computer-based techniques to compute the registration between pre-operative CT or MR and intra-operative ultrasound are advantageous. However, computer-based registration of pre-operative volumes (such as CT or MR) to intra-operative ultrasound volumes is a challenging task due to organ deformation which occurs as a result of soft tissue motion, for example from the application of the ultrasound probe, such that correspondence between features in the pre-operative volumes and features in the ultrasound volumes can be difficult to achieve.

BRIEF SUMMARY OF THE INVENTION

The present invention provides a method and system for registration of pre-operative volumetric medical images to intra-operative ultrasound images. Embodiments of the present invention register pre-operative volumetric medical images and intra-operative ultrasound images using a biomechanically driven image registration based on both B-mode ultrasound and ultrasound elastography.

In an embodiment of the present invention, a method for registering a pre-operative 3D medical image volume of a target organ to intra-operative ultrasound images comprises: acquiring an intra-operative 3D B-mode ultrasound volume and an intra-operative 3D ultrasound elastography volume; determining patient-specific boundary conditions for a bio-mechanical tissue model of a target organ using the intra-operative 3D B-mode volume; determining patient-specific material properties for the biomechanical tissue model of the target organ using the 3D ultrasound elastography volume; and deforming the target organ in the pre-operative 3D medical image volume using the biomechanical tissue model with the patient-specific material properties with the deformation of the target organ in the pre-operative 3D medical image volume constrained by the patient-specific boundary conditions.

In an embodiment, acquiring an intra-operative 3D B-mode ultrasound volume and an intra-operative 3D ultrasound elastography volume comprises: simultaneously acquiring a stream of 2D B-mode ultrasound images and a stream of 3D ultrasound elastography images by interleaving frames acquired using a B-mode ultrasound acquisition protocol and frames acquired using an ultrasound elastography acquisition protocol during a sweep of the target organ with an ultrasound probe; generating the intra-operative 3D B-mode ultrasound volume by compounding the stream of 2D B-model ultrasound images; and generating the intra-operative 3D ultrasound elastography volume by compounding the stream of 2D ultrasound elastography images.

In an embodiment, the method further comprises tracking the ultrasound probe in 3D space using a tracking system, resulting in tracking information associated with each frame acquired by the ultrasound probe, wherein the intra-operative 3D B-mode ultrasound volume is generated by compounding the stream of 2D B-model ultrasound images using the tracking information associated each frame of the stream of 2D B-model ultrasound images and the intra-operative 3D ultrasound elastography volume is generated by compounding the stream of 2D ultrasound elastography images using the tracking information associated each frame of the stream of 2D ultrasound elastography images.

In an embodiment, acquiring an intra-operative 3D B-mode ultrasound volume and an intra-operative 3D ultrasound elastography volume comprises acquiring the intra-operative 3D B-mode ultrasound volume and the intra-operative ultrasound elastography volume using a 3D ultrasound probe.

In an embodiment, the biomechanical tissue model is constructed on an a pre-operative tissue domain defined by a segmentation of the target organ in the pre-operative medical image volume, and determining patient-specific boundary conditions for a bio-mechanical tissue model of a target organ using the intra-operative 3D B-mode volume comprises: establishing surface correspondences on a surface of the target organ segmented in the pre-operative medical image volume and a surface of the target organ segmented in the intra-operative 3D B-mode ultrasound volume; and designating boundary conditions for the bio-mechanical tissue model that constrain the deformation of the target organ in the pre-operative 3D medical image volume based on displacements between the surface correspondences on the surface of the target organ segmented in the pre-operative medical image volume and the surface of the target organ segmented in the intra-operative 3D B-mode ultrasound volume.

In an embodiment, determining patient-specific material properties for the biomechanical tissue model of the target organ using the 3D ultrasound elastography volume comprises: (a) warping the pre-operative tissue domain using the bio-mechanical tissue model with a current tissue material property distribution for the pre-operative tissue domain based on the patient-specific boundary conditions, resulting in a model-deformed distribution of the tissue material property; (b) calculating an incremental update to the tissue material property distribution based on a difference between the model-deformed distribution of the tissue material property and a distribution of the tissue material property in the intra-operative 3D ultrasound elastography volume; and (c) updating the current tissue material property distribution for the pre-operative tissue domain based on the calculated incremental update to the tissue material property distribution.

In an embodiment, determining patient-specific material properties for the biomechanical tissue model of the target organ using the 3D ultrasound elastography volume further comprises: repeating steps (a), (b), and (c) for a plurality of iterations.

In an embodiment, repeating steps (a), (b), and (c) for a plurality of iterations comprises repeating steps (a), (b), and (c) for a plurality of iterations until the difference between the model-deformed distribution of the tissue material property and the distribution of the tissue material property in the intra-operative 3D ultrasound elastography volume is less than a threshold value.

In an embodiment, repeating steps (a), (b), and (c) for a plurality of iterations comprises repeating steps (a), (b), and (c) for a plurality of iterations until a predetermined maximum number of iterations is reached.

In an embodiment, the tissue material property distribution is a tissue stiffness distribution.

In an embodiment, deforming the target organ in the pre-operative 3D medical image volume using the biomechanical tissue model with the patient-specific material properties with the deformation of the target organ in the pre-operative 3D medical image volume constrained by the patient-specific boundary conditions comprises: deforming the target organ in the pre-operative 3D medical image volume using the biomechanical tissue model with the current tissue material property distribution for the pre-operative tissue domain resulting from a final iteration of the plurality of iterations with the deformation of the target organ in the pre-operative 3D medical image volume constrained by the patient-specific boundary conditions.

In an embodiment, the method further comprises: performing an initial rigid alignment of the pre-operative medical image volume and the intra-operative 3D B-mode ultrasound volume prior to determining the patient-specific boundary conditions, determining the patient-specific material properties, and deforming the target organ in the pre-operative 3D medical image volume using the biomechanical tissue model.

In an embodiment, the method further comprises: overlaying the deformed target organ in the pre-operative 3D medical image volume on at least one of the intra-operative 3D B-mode ultrasound volume or one or more intra-operative 2D B-mode ultrasound images.

In an embodiment, the method further comprises: deforming a map of target points defined for the target organ in the pre-operative medical image volume using a non-rigid transformation corresponding to the deformation of the target organ in the pre-operative 3D medical image volume using the biomechanical tissue model; and overlaying the deformed map of target points defined for the target organ on at least one of the intra-operative 3D B-mode ultrasound volume or one or more intra-operative 2D B-mode ultrasound images.

In an embodiment, the method further comprises: mapping the B-mode ultrasound image to a coordinate system of the pre-operative medical image volume based on a non-rigid transformation corresponding to the deformation of the target organ in the pre-operative 3D medical image volume using the biomechanical tissue model.

In an embodiment, the pre-operative medical image volume is one of a computed tomography volume or a magnetic resonance imaging volume.

In an embodiment, the target organ is one of a liver or a prostate.

In an embodiment of the present invention, an apparatus for registering a pre-operative 3D medical image volume of a target organ to intra-operative ultrasound images, comprises a processor and a memory storing computer program instructions, which when executed by the processor cause the processor to perform operations comprising: acquiring an intra-operative 3D B-mode ultrasound volume and an intra-operative 3D ultrasound elastography volume; determining patient-specific boundary conditions for a biomechanical tissue model of a target organ using the intra-operative 3D B-mode volume; determining patient-specific material properties for the biomechanical tissue model of the target organ using the 3D ultrasound elastography volume; and deforming the target organ in the pre-operative 3D medical image volume using the biomechanical tissue model with the patient-specific material properties with the deformation of the target organ in the pre-operative 3D medical image volume constrained by the patient-specific boundary conditions.

In an embodiment of the present invention, a non-transitory computer readable medium stores computer program instructions for registering a pre-operative 3D medical image volume of a target organ to intra-operative ultrasound images. The computer program instructions, when executed by a processor, cause the processor to perform operations comprising: acquiring an intra-operative 3D B-mode ultrasound volume and an intra-operative 3D ultrasound elastography volume; determining patient-specific boundary conditions for a biomechanical tissue model of a target organ using the intra-operative 3D B-mode volume; determining patient-specific material properties for the biomechanical tissue model of the target organ using the 3D ultrasound elastography volume; and deforming the target organ in the pre-operative 3D medical image volume using the biomechanical tissue model with the patient-specific material properties with the deformation of the target organ in the pre-operative 3D medical image volume constrained by the patient-specific boundary conditions.

These and other advantages of the invention will be apparent to those of ordinary skill in the art by reference to the following detailed description and the accompanying drawings.

DETAILED DESCRIPTION

The present invention relates to a method and system for computer-based registration of pre-operative volumetric medical images to intra-operative ultrasound images. Embodiments of the present invention are described herein to give a visual understanding of the registration method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

The task of computer-based registration/fusion of pre-operative medical imaging data, such as computed tomography (CT) or magnetic resonance (MR), and intra-operative ultrasound (US) is difficult due to non-rigid tissue deformation of anatomical structures which occurs between the imaging sessions and the lack of known feature correspondences. One simple existing technique for registering pre-operative medical imaging data and intra-operative US involves computing a rigid transformation to align the target organ using point or surface features. However, a rigid transformation is typically insufficient to accurately align organ structures in the pre-operative medical image data and the intra-operative US due to soft tissue deformation which occurs during US imaging. More sophisticated methods utilize some kind of deformable registration, such as a biomechanical tissue model. However, existing biomechanical modeling approaches for registering pre-operative medical imaging data and intra-operative US do not utilize patient-specific material properties. Embodiments of the present invention provide an improvement over existing methods for registering pre-operative medical images an intra-operative US images by using a biomechanical tissue model with patient-specific boundary conditions and patient-specific material properties for the biomechanical model being automatically determined from compounded B-mode US and ultrasound elastography (USE) image streams. This provides an advantage of improved accuracy as compared with previous registration techniques. In addition, embodiments of the present invention provide an improvement of generating the two US images streams by interleaving the B-mode and USE image frames while sweeping the target organ intra-operatively, so that the two US image streams are implicitly co-registered due to the high sampling rate of US.

Computer-based registration of pre-operative medical imaging volumes, such as CT or MR volumes, to 3D ultrasound volumes is a challenging task due to organ deformation which occurs as a result of soft tissue motion, for example due to the application of the US probe, such that correspondence between features in the pre-operative volume and the US volume can be difficult to achieve. According to an advantageous embodiment of the present invention, this registration/fusion or a pre-operative medical imaging volume and an intra-operative US volume can be performed in two phases of: 1) an initial rigid alignment, and 2) a non-rigid alignment/deformation. Embodiments of the present invention perform the non-rigid deformation by establishing point-based correspondences between geometry of a target organ in the pre-operative medical imaging volume and geometry of the target organ from an intra-operative B-mode US volume and then deforming the pre-operative organ geometry using a biomechanical tissue model while constraining the deformation such that the correspondences in the deformed pre-operative organ geometry match those in the B-mode US volume. Embodiments of the present invention utilize patient-specific tissue stiffness values for the biomechanical tissue model, which are acquired from a 3D USE volume and used to guide the model deformation.

Figure 1:
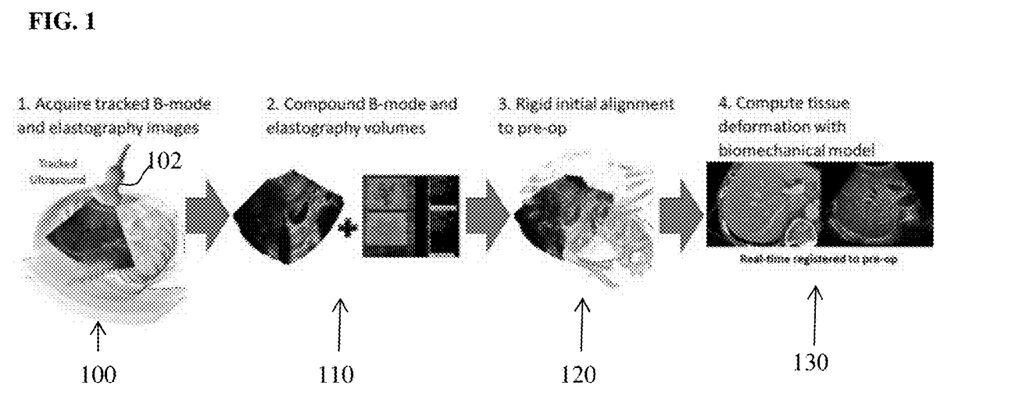
FIG. 1 illustrates an overview of an intra-operative workflow for registering a pre-operative medical imaging volume to intra-operative ultrasound (US) images according to an embodiment of the present invention.

In an embodiment of the present invention, the computer-based registration method takes as input a pre-operative medical image volume (e.g., CT or MR) and a set of tracked ultrasound frames and outputs a non-rigid transformation which encodes the alignment of the pre-operative medical image data with the intra-operative ultrasound data, which can be used to enable fused image displays in real-time during an intervention procedure. FIG. 1 illustrates an overview of an intra-operative workflow for registering a pre-operative medical imaging volume to intra-operative US images according to an embodiment of the present invention. As illustrated in the embodiment of FIG. 1, at step 100, tracked B-mode US images and US electrography (USE) images are acquired. In an advantageous implementation, a user sweeps a tracked ultrasound probe 102 across a target organ to acquire 2D B-mode US images and 2D USE images. The B-mode US images and USE images can be acquired simultaneously by the US probe 102 acquiring an interleaved stream of B-mode and USE images during the sweep. Due to the high sampling rate of US, this results in compounded B-mode and USE volumes that are implicitly co-registered. The US probe 102 is tracked in 3D space using a tracking system. For example, an optical tracker or electromagnetic tracker may be used to track the 3D position and orientation of the US probe 102. At step 110, the B-mode images are compounded based on the tracking information to generate a 3D B-mode US volume and the USE images are compounded to generate a 3D USE volume. At step 120, an initial rigid alignment between the pre-operative medical image volume and the 3D B-mode US volume is calculated. At step 130, the tissue deformation of the target organ in the pre-operative medical image volume is computed to using a biomechanical tissue model to non-rigidly register the pre-operative medical image data to the intra-operative US data. Patient-specific boundary conditions for the biomechanical tissue model that are used to constrain the deformation of the pre-operative target are determined using the 3D B-mode US volume. Patient-specific material properties, such as a spatially varying distribution of tissue stiffness values, are determined using the 3D USE volume.

Figure 2:
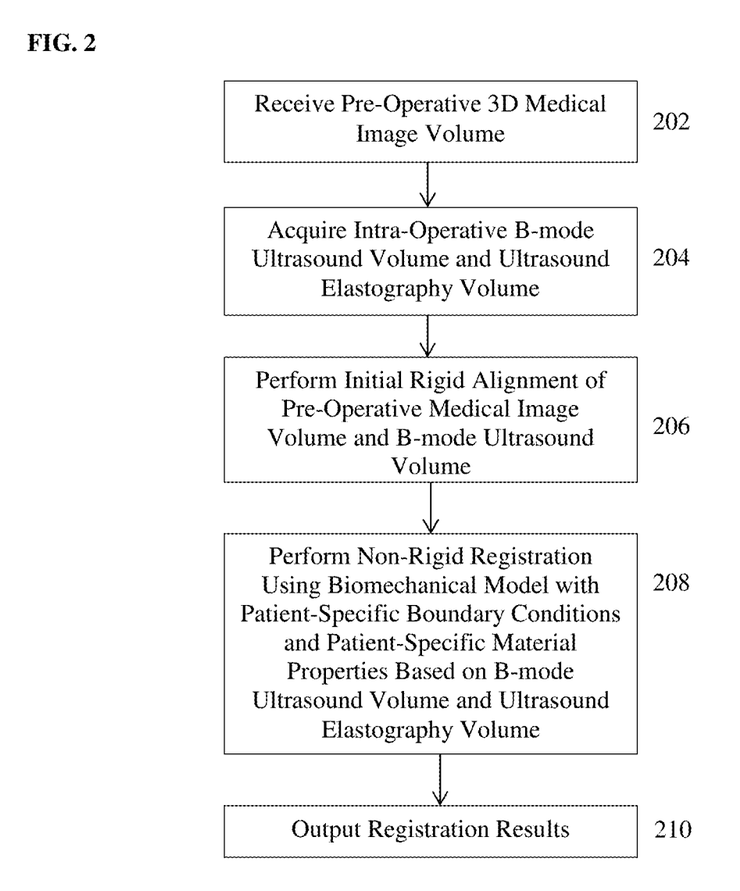
FIG. 2 illustrates a method for registering pre-operative medical image date and intra-operative US data according to an embodiment of the present invention.

FIG. 2 illustrates a method for registering pre-operative medical image date and intra-operative US data according to an embodiment of the present invention. The method of FIG. 2 can be used to provide computer-based registration and fusion of pre-operative medical image data and intra-operative US data during an US guided intervention on a target organ. In exemplary embodiments, the target organ may be the liver or the prostate, but the present invention is not limited thereto and may be used for any organ for which an US guided intervention is performed. Examples of US guided interventions for which this method may be applied include US guide staging for liver lesion resection and US guided prostate needle biopsies, but the present invention is not limited thereto.

Referring to FIG. 2, at step 202, a pre-operative medical image volume of the target organ of the patient is received. The pre-operative medical image volume typically provides dense anatomical or functional data. In an advantageous implementation, the pre-operative 3D medical image volume is acquired prior to the surgical procedure. The 3D medical image volume can be acquired using any imaging modality, such as computed tomography (CT), magnetic resonance (MR), or positron emission tomography (PET). The pre-operative 3D medical image volume can be received directly from an image acquisition device, such as a CT scanner or MR scanner, or can be received by loading a previously stored 3D medical image volume from a memory or storage of a computer system. In a possible implementation, in a pre-operative planning phase, the pre-operative 3D medical image volume can be acquired using the image acquisition device and stored in the memory or storage of the computer system. The pre-operative 3D medical image can then be loaded from the memory or storage system during the surgical procedure. In another possible implementation, the pre-operative medical image volume may be acquired directly before or even during a procedure, for example using a C-arm image acquisition device or intra-operative MR.

The pre-operative 3D medical image volume includes a target anatomical object, such as a target organ. For example, the target organ can be the liver or the prostate. The pre-operative volumetric imaging data can provide for a more detailed view of the target anatomical object, as compared to intra-operative US images. The target organ is segmented in the pre-operative 3D medical image volume and used to construct of 3D point representation in the tissue domain in the pre-operative coordinates, typically as a mesh or a 3D point cloud. The 3D point representation is used to define the domain of the biomechanical tissue model. A machine learning based segmentation algorithm may be used to segment the target organ in the pre-operative medical image volume. In one embodiment, a marginal space learning (MSL) based framework may be employed, e.g., using the method described in U.S. Pat. No. 7,916,919, entitled "System and Method for Segmenting Chambers of a Heart in a Three Dimensional Image," which is incorporated herein by reference in its entirety. In another embodiment, a semi-automatic segmentation technique, such as, e.g., graph cut or random walker segmentation can be used. In another embodiment, a deep-learning based segmentation technique can be used, such as a deep-learning based segmentation technique described in International Patent Publication No. WO 2018/015414 A1, entitled "Method and System for Artificial Intelligence Based Medical Image Segmentation," which is incorporated herein by reference in its entirety.

At step 204, an intra-operative 3D B-mode US volume and an intra-operative 3D USE volume are acquired. In one embodiment, the intra-operative 3D B-mode US volume and an intra-operative 3D USE volume can be acquired by acquiring a stream of intra-operative 2D B-mode US images and a stream of intra-operative 2D USE images using a tracked US probe and generating the intra-operative 3D B-mode US volume and intra-operative 3D USE volume by compounding the 2D B-mode US images and the 2D USE images, respectively. Any type of US probe can be used to acquire the intra-operative US images, depending on the target organ. For example, the US probe may be an external US probe, an intravascular ultrasound (IVUS) probe, an endorectal ultrasound (ERUS) probe, etc. A tracking system is used to track the US probe in 3D space. For example, an optical tracker or an electromagnetic tracker can be used to track the US probe. The tracking system providing tracking information corresponding to the position and orientation of the US probe for each frame (US image) acquired by the US probe. A sweep of the target organ is performed using the US probe to obtain a stream of 2D US images that cover the target organ. In an advantageous embodiment, the stream of 2D B-mode US images and the stream of 2D USE images are acquired simultaneously in a single interleaved stream by the US probe during the sweep of the target organ. In particular, the US probe interleaves the B-mode frame acquisition protocol and the USE frame acquisition protocol, such that the stream of US images received from the US probe alternates B-mode and USE frames. The intra-operative 3D B-mode US volume is generated by compounding the stream of 2D B-mode US images based on the tracking information associated with the 2D B-mode US images. The intra-operative 3D USE volume is generated by compounding the stream of 2D USE images based on the tracking information associated with the 2D USE images.

In another embodiment, the US probe may be a 3D US probe that acquires 3D US volumes. In this case, the intra-operative 3D B-mode US volume and intra-operative 3D USE volume are received from the US probe, which captures the intra-operative 3D B-mode US volume and the intra-operative 3D USE volume as native 3D volumes.

At step 206, an initial rigid alignment of the pre-operative medical image volume and the intra-operative 3D B-mode US volume is performed. The target organ is segmented in the 3D B-mode US volume to provide a 3D point representation of the target organ in the US coordinates. The segmented 3D point representation can be a 3D mesh or a 3D point cloud. A machine learning based segmentation algorithm or any other segmentation algorithm may be used to segment the target organ in the 3D B-mode US volume. In one embodiment, a marginal space learning (MSL) based framework may be employed, e.g., using the method described in U.S. Pat. No. 7,916,919, entitled "System and Method for Segmenting Chambers of a Heart in a Three Dimensional Image," which is incorporated herein by reference in its entirety. In another embodiment, a semi-automatic segmentation technique, such as, e.g., graph cut or random walker segmentation can be used. In another embodiment, a deep-learning based segmentation technique can be used, such as a deep-learning based segmentation technique described in International Patent Publication No. WO 2018/015414 A1, entitled "Method and System for Artificial Intelligence Based Medical Image Segmentation," which is incorporated herein by reference in its entirety. The initial rigid alignment may be performed using known rigid registration techniques to find a rigid registration that minimizes differences between corresponding point or surface features on the segmented target organ in the pre-operative medical image volume and the segmented target organ in the intra-operative 3D USE volume.

At step 208, non-rigid registration is performed using a biomechanical tissue model with patient-specific boundary conditions and patient-specific material properties based on the intra-operative 3D B-mode US volume and the intra-operative 3D USE volume. The biomechanical tissue model simulates biomechanical deformation of the tissue of the target organ. According to an embodiment of the present invention, the biomechanical tissue model is used to drive the non-rigid registration by computing deformation between the target organ in the pre-operative medical image volume and the intra-operative US acquisition. Patient-specific boundary conditions for the biomechanical tissue model are computed based on the intra-operative 3D USE volume and are used to constrain the simulated deformation of the pre-operative target organ such that positions of surface correspondences match on the deformed pre-operative target organ and the intra-operative target organ. Patient-specific material properties for the biomechanical tissue model, such as a distribution of spatially varying values of a tissue property, are determined for the pre-operative tissue domain based on the intra-operative 3D USE volume. In an advantageous embodiment, a distribution of tissue stiffness (Young's modulus) is determined for the pre-operative tissue domain based on the intra-operative 3D USE volume. This increases accuracy of the biomechanical tissue model driven deformation computed for the target organ in the pre-operative domain to non-rigidly register the target organ segmented in the pre-operative medical image volume with the target organ segmented in the intra-operative 3D B-mode US volume.

Figure 3:
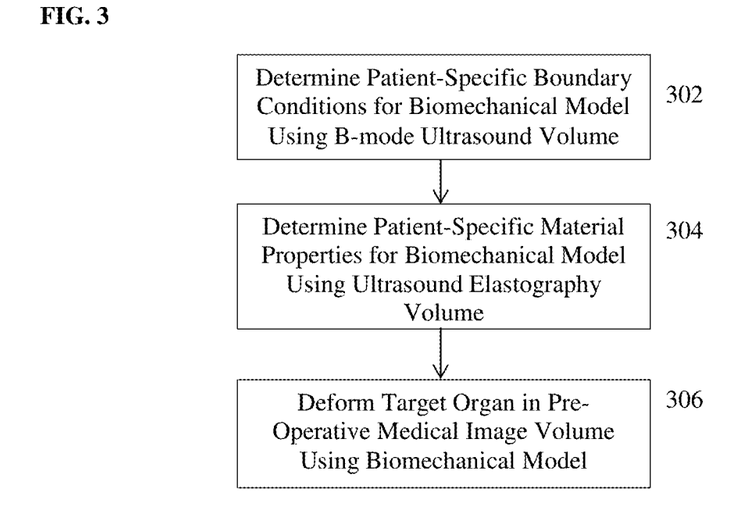
FIG. 3 illustrates a method of determining patient-specific boundary conditions and material properties for a biomechanical tissue model of a target organ and performing non-rigid registration driven by the biomechanical tissue model according to an embodiment of the present invention.

FIG. 3 illustrates a method of determining patient-specific boundary conditions and material properties for a biomechanical tissue model of a target organ and performing non-rigid registration driven by the biomechanical tissue model according to an embodiment of the present invention. The method of FIG. 3 can be used to implement step 208 of FIG. 2.

Referring to FIG. 3, at step 302, patient-specific boundary conditions are determined for the biomechanical tissue model using the intra-operative 3D B-mode US volume. According to an advantageous implementation, point correspondences between the target organ segmentations in the pre-operative medical image volume and the 3D B-mode US volume are used as boundary conditions to the biomechanical tissue model. In an advantageous embodiment, the biomechanical tissue model is implemented using a finite element model (FEM) solution for the equations of motions describing the organ deformation. The organ domain for the biomechanical tissue model is discretized as a tetrahedral mesh from the geometry of the segmented surface of the target organ in the pre-operative medical image volume. The biomechanical tissue model can use 3D Navier-Cauchy equations for the tissue displacement field at static equilibrium:

$$\frac{E}{2(1+\upsilon)(1-2\upsilon)}\nabla(\nabla\cdot\mu)+\frac{E}{2(1+\upsilon)}\nabla^2\mu+F=0 \quad (1)$$

where E is Young's modulus, $\upsilon$ is Poisson's ratio, $\mu$ is the 3D displacement vector at a point in the tissue, and F is the applied body force distribution. The biomechanical tissue model seeks to solve for the displacements at each point of the tissue domain such that this equation is satisfied. In an advantageous implementation, linear basis functions define on the tetrahedral elements of the target organ mesh (in the pre-operative domain) can be used and the Galerkin weighted residual method can be performed to construct a linear system of equations with the form:

$$K\mu=f \quad (2)$$

where K is the stiffness matrix containing contributions from the material properties and constitutive equation (1), $\mu$ is the vector of mesh nodal displacements, and f contains a vector of applied boundary conditions. According to an advantageous embodiment of the present invention, patient-specific boundary conditions for f are generated using the information in the B-mode US volume and also patient-specific material properties are generated using the information in the USE volume.

In order to determine the patient-specific boundary conditions, displacement conditions are calculated for boundary nodes in f based on vectors mapping from boundary point locations in the segmentation of the target organ in the pre-operative medical image volume to the locations of the corresponding boundary points in the segmentation of the target organ in the inter-operative 3D B-mode US volume. The displacement boundary conditions known from these segmentation correspondences are assigned by modifying the appropriate equations in equation (2) to give a final system of equations:

$$A\mu=b \quad (3)$$

which is solved for the nodal displacements which satisfy the boundary conditions and material properties. By defining the displacement boundary conditions using displacements between point/surface correspondences (i.e., corresponding boundary nodes) on the pre-operative target organ segmentation and the intra-operative target organ segmentation, and solving for the nodal displacements which satisfy these boundary conditions, the boundary conditions constrain the deformation of the pre-operative target organ computed by the biomechanical tissue model such that the locations of the point/surface correspondences of the deformed pre-operative target organ match those on the intra-operative target organ.

At step 304, patient-specific material properties are determined using the intra-operative 3D USE volume. The material property distribution in the pre-operative imaging is typically unknown and must be guessed initially. For example, a homogenous material property (e.g., Young's modulus) distribution using a value for the target organ from literature may be used as an initial material property distribution for the target organ in the pre-operative medical image volume. The patient-specific boundary conditions (determined using the intra-operative B-mode US volume in step 302) are then used in biomechanical tissue model to warp the pre-operative tissue domain to match the US coordinates, after which the warped pre-operative tissue distribution of the tissue properties can be directly compared to the known tissue property distribution in the intra-operative 3D USE volume. The pre-operative properties are then updated to better match the data in the 3D USE volume and the model deformation is recomputed using the updated pre-operative tissue property distribution. These steps can be iterated until the warped pre-operative tissue property distribution matches the spatial distribution of the tissue property in the USE volume.

Figure 4:
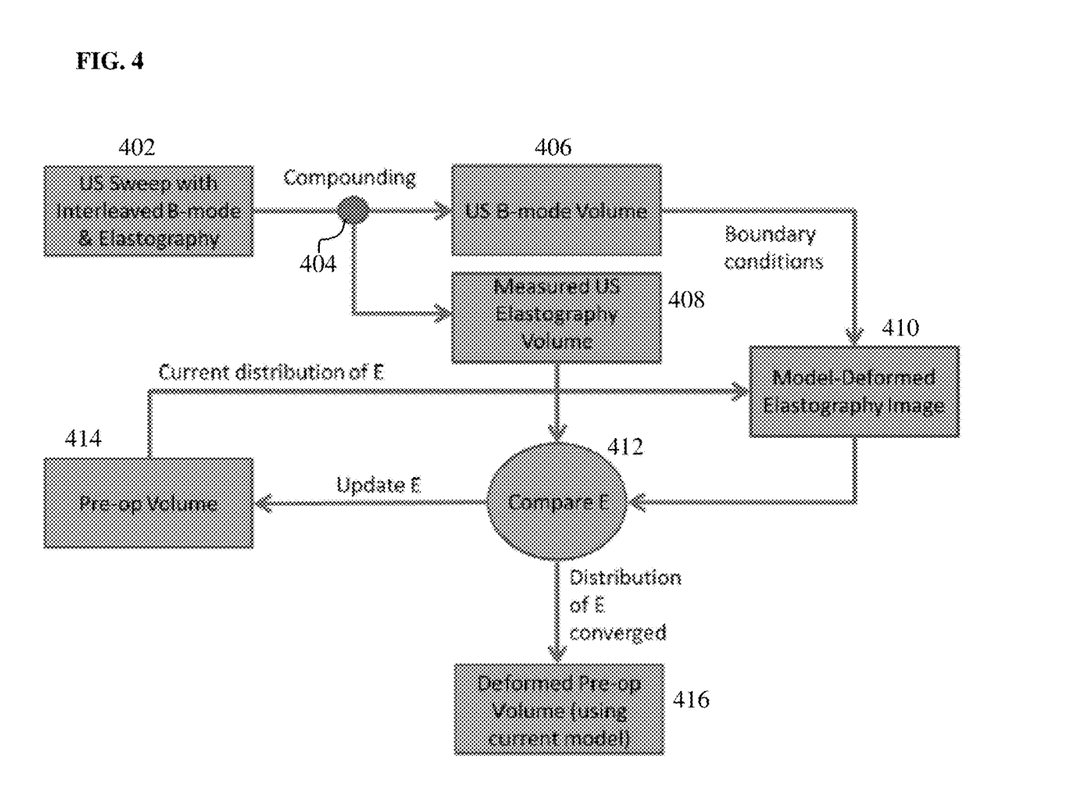
FIG. 4 illustrates a method of iteratively computing a patient-specific material property distribution according to an embodiment of the present invention.

FIG. 4 illustrates a method of iteratively computing a patient-specific material property distribution according to an embodiment of the present invention. In the embodiment of FIG. 4, a patient-specific distribution of tissue stiffness (i.e., Young's modulus) is computed for the target organ. In the embodiment illustrated in FIG. 4, at step 402, an US sweep is performed with interleaved B-mode and USE frame acquisition protocols in order to acquire a stream of 2D B-mode US images and a stream of 2D USE images. At step 404, the 2D B-mode images are compounded to generate the 3D US B-mode volume 406 and the 2D USE images are compounded to generate the 3D USE volume 408. Prior to computing the patient-specific stiffness property distribution for the biomechanical tissue model, the patient-specific boundary conditions are computed based on the US B-mode volume 406, as described above in connection with step 302 of FIG. 3. Steps 410, 412, and 414 of FIG. 4 are then iterated to compute the patient-specific stiffness property distribution for the pre-operative tissue domain.

At step 410, a model-deformed elastography image is generated by warping the current distribution for the stiffness property in the pre-operative tissue domain using the biomechanical model based on the patient-specific boundary conditions. The first time step 410 is performed, a predetermined initial tissue stiffness distribution can be used to initialize the tissue stiffness distribution in the pre-operative tissue domain. For example, the initial tissue stiffness distribution may be a uniform distribution with a value for tissue stiffness selected from literature used at all spatial locations (nodes) of the pre-operative tissue domain. The embodiment of FIG. 4 shows the example of solving for the distribution of Young's modulus, E. Let $E_p^i$, be the current guess for the stiffness distribution in the pre-operative domain at iteration i. Then the model-deformed distribution (i.e., model-deformed elastography image) $E_d^i$ is computed as:

$$E_d^i = T(E_p^i, \theta^i) \quad (4)$$

where T is the warping operation using the model displacement field and $\theta^i$ includes all other parameters in the model (boundary conditions, etc.). Accordingly, in this step, the biomechanical model and boundary conditions are used to warp the current guess for the tissue stiffness distribution in the pre-operative domain to the coordinate system of the US.

At step 412, the model-deformed tissue stiffness distribution is compared to the measured USE volume 408. A difference $\Delta E^i$ between the model-deformed tissue stiffness distribution $E_d^i$ and the tissue stiffness distribution in the USE volume is computed as:

$$\Delta E^i = E_d^i - E_a^i \quad (5)$$

where $E_a^i$ is the actual stiffness distribution in the intra-operative 3D USE volume.

At step 414, the current tissue stiffness distribution in the domain of the pre-operative medical image volume is updated based on the difference $\Delta E^i$ between the model-deformed tissue stiffness distribution and the actual tissue stiffness distribution in the USE volume. In an advantageous implementation, the following schema is used to compute an incremental update for the tissue stiffness distribution:

$$E_u^i = k_1 \Delta E^i + k_2 (\Delta E^i - \Delta E^{i-1}) \quad (6)$$

where the parameters $k_1$ and $k_2$ are selected to control convergence speed and stability of the algorithm. The tissue stiffness distribution in the pre-operative model domain is then updated to set the tissue stiffness distribution in the pre-operative domain for the next iteration as:

$$E_p^{i+1} = T^{-1}(E_p^i + E_u^i, \theta^i). \quad (7)$$

The method then returns to step 410 and repeats steps 410, 412, and 414 until a stop condition indicating convergence of the tissue stiffness distribution is reached. In particular, in each iteration at step 412, it is determined whether a stop condition is reached. For example, the stop condition can be reached when the difference $\Delta E^i$ between the model-deformed tissue stiffness distribution and the actual tissue stiffness distribution in the USE volume is less than a certain threshold value. Alternatively, the stop condition can be reached when the difference between a predetermined maximum number of iterations has been reached. If the stop condition is not yet reaches, the method continues to step 414 and performs another iteration. When the stop condition has been reached, it is determined that the tissue stiffness distribution in the pre-operative tissue domain has converged to the final patient-specific tissue stiffness values, and the method proceeds to step 416, at which at least a portion of the pre-operative medical image volume is deformed using the biomechanical model with the patient-specific boundary conditions and the patient-specific stiffness values.

Returning to FIG. 3, at step 306, the target organ in the pre-operative medical image volume is deformed using the biomechanical model with the patient-specific material properties (determined in step 304) and the patient-specific boundary conditions (determined in step 302). Once the patient-specific boundary conditions and the patient-specific material properties are determined, the biomechanical tissue model with the patient-specific material properties and the patient-specific boundary conditions is used to perform a final biomechanical warping of the pre-operative data. The nodal displacements from the biomechanical model solution provide a non-rigid transformation which describes the organ deformation between the pre-operative and US imaging scans.

Returning to FIG. 2, at step 210, the registration results are output. Once the non-rigid registration is performed using the biomechanical tissue model, the resulting non-rigid transformation can be used to transform the target organ structure from the pre-operative medical image volume to the coordinate system of the intra-operative US scans. The transformed target organ from the pre-operative medical image volume can then be overlaid on the 3D B-mode US volume or on one or more 2D US images acquired during the US guided intervention. In an exemplary implementation, the target organ can be automatically overlaid on newly acquired intra-operative US images in real time as the US images are acquired by the US probe using the non-rigid transformation. The displacement field computed for the target organ can also be used to target maps of the target organ, such as maps of suspected nodules or planning annotations, from the pre-operative coordinate system to the US coordinate system to overlay such target maps on the 3D B-mode US volume or on one or more 2D US images acquired during the US guided intervention. Such target maps may be automatically overlaid on 2D US images as the US images are acquired. The displacements may also be used to directly warp image information itself from the pre-operative medical image volume to be overlaid on the 3D B-mode US volume or on one or more 2D US images. An inverse of the computed non-rigid transformation may be used to transform the target organ and/or image data from the US scans to the coordinate system of the pre-operative medical image volume to be overlaid on the pre-operative medical image volume. Fused images resulting from overlaying information from the pre-operative medical image data onto the US images or from overlying information from the intra-operative US data onto the pre-operative medical image data can be displayed on a display device of a computer system and used to guide the US guide intervention.

Figure 5:
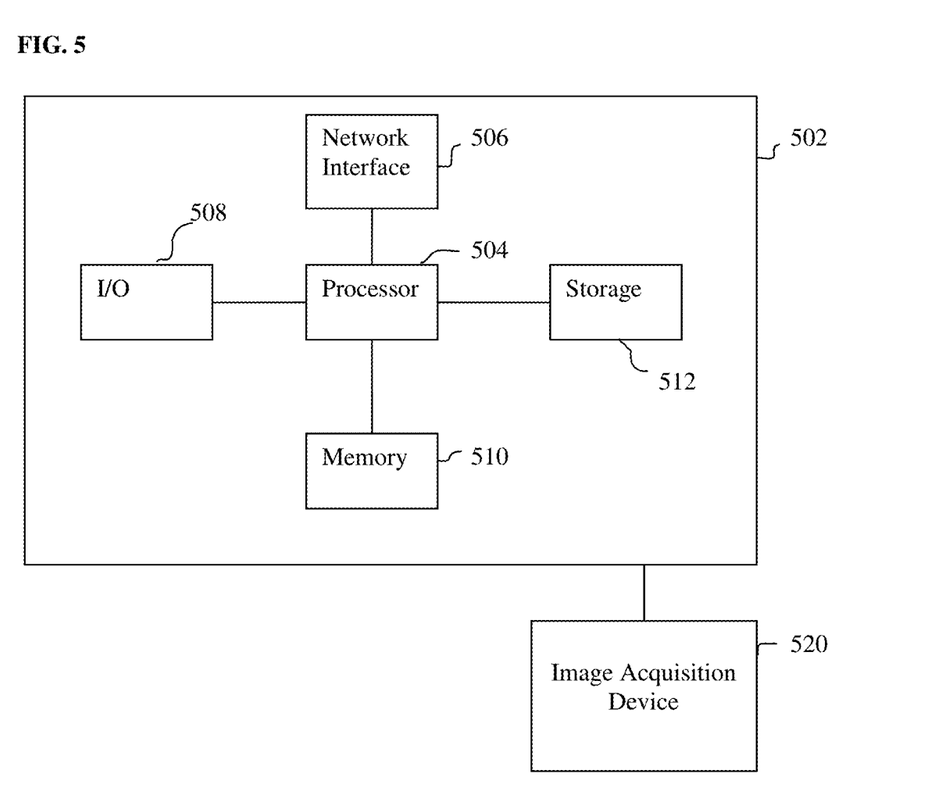
FIG. 5 is a high-level block diagram of a computer capable of implementing the present invention.

The above-described methods for registering a pre-operative volumetric medical image data to intra-operative US image data may be implemented on a computer using well-known computer processors, memory units, storage devices, computer software, and other components. A high-level block diagram of such a computer is illustrated in FIG. 5. Computer 502 contains a processor 504, which controls the overall operation of the computer 502 by executing computer program instructions which define such operation. The computer program instructions may be stored in a storage device 512 (e.g., magnetic disk) and loaded into memory 510 when execution of the computer program instructions is desired. Thus, the steps of the methods of FIGS. 1, 2, 3, and 4 may be defined by the computer program instructions stored in the memory 510 and/or storage 512 and controlled by the processor 504 executing the computer program instructions. One or more image acquisition device 520, such as an ultrasound probe, CT scanner, MR scanner, PET scanner, etc., can be connected to the computer 502 to input image data to the computer 502. It is possible that the image acquisition device 520 and the computer 502 communicate wirelessly through a network. The computer 502 also includes one or more network interfaces 506 for communicating with other devices via a network. The computer 502 also includes other input/output devices 508 that enable user interaction with the computer 502 (e.g., display, keyboard, mouse, speakers, buttons, etc.). Such input/output devices 508 may be used in conjunction with a set of computer programs as an annotation tool to annotate volumes received from the image acquisition device 520. One skilled in the art will recognize that an implementation of an actual computer could contain other components as well, and that FIG. 5 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for registering a pre-operative 3D medical image volume of a target organ to intra-operative ultrasound images, comprising:
    acquiring an intra-operative 3D B-mode ultrasound volume and an intra-operative 3D ultrasound elastography volume by acquiring and interleaving a stream of 2D B-mode ultrasound images and a stream of 2D ultrasound elastography images;
    determining patient-specific boundary conditions for a biomechanical tissue model of a target organ using the intra-operative 3D B-mode ultrasound volume, wherein the biomechanical tissue model is constructed on a pre-operative tissue domain defined by a segmentation of the target organ in the pre-operative 3D medical image volume, the patient-specific boundary conditions determined by:
        establishing surface correspondences on a surface of the target organ segmented in the pre-operative 3D medical image volume and a surface of the target organ segmented in the intra-operative 3D B-mode ultrasound volume; and
        designating boundary conditions for the biomechanical tissue model that constrain deformation of the target organ in the pre-operative 3D medical image volume based on displacements between the surface correspondences on the surface of the target organ segmented in the pre-operative 3D medical image volume and the surface of the target organ segmented in the intra-operative 3D B-mode ultrasound volume;
    determining patient-specific material properties for the biomechanical tissue model of the target organ using the intra-operative 3D ultrasound elastography volume by:
        warping the pre-operative tissue domain using the biomechanical tissue model based on the patient-specific boundary conditions to warp a current tissue material property distribution, the pre-operative tissue domain warped such that locations of the surface correspondences on the target organ in the pre-operative 3D medical image volume match the surface correspondences on the target organ in the intra-operative 3D B-mode ultrasound volume,
        comparing the warped current tissue material property distribution with a measured tissue material property distribution measured from the intra-operative 3D ultrasound elastography volume, and
        updating the current tissue material property distribution based on the comparison, wherein the patient-specific material properties include a distribution of spatially varying values of a tissue property; and
    deforming the target organ in the pre-operative 3D medical image volume using the biomechanical tissue model with the patient-specific material properties, wherein the deformation of the target organ in the pre-operative 3D medical image volume is constrained by the patient-specific boundary conditions.

2. The method of claim 1, wherein acquiring an intra-operative 3D B-mode ultrasound volume and an intra-operative 3D ultrasound elastography volume comprises:
    interleaving frames acquired using a B-mode ultrasound acquisition protocol and frames acquired using an ultrasound elastography acquisition protocol during a sweep of the target organ with an ultrasound probe;
    generating the intra-operative 3D B-mode ultrasound volume by compounding the stream of 2D B-mode ultrasound images; and
    generating the intra-operative 3D ultrasound elastography volume by compounding the stream of 2D ultrasound elastography images.

3. The method of claim 2, further comprising:
    tracking the ultrasound probe in 3D space using a tracking system, resulting in tracking information associated with each frame acquired by the ultrasound probe, wherein the intra-operative 3D B-mode ultrasound volume is generated by compounding the stream of 2D B-mode ultrasound images using the tracking information associated with each frame of the stream of 2D B-mode ultrasound images and the intra-operative 3D ultrasound elastography volume is generated by compounding the stream of 2D ultrasound elastography images using the tracking information associated with each frame of the stream of 2D ultrasound elastography images.

4. The method of claim 1, wherein acquiring an intra-operative 3D B-mode ultrasound volume and an intra-operative 3D ultrasound elastography volume comprises:
    acquiring the intra-operative 3D B-mode ultrasound volume and the intra-operative 3D ultrasound elastography volume using a 3D ultrasound probe.

5. The method of claim 1, wherein determining patient-specific material properties for the biomechanical tissue model of the target organ using the intra-operative 3D ultrasound elastography volume further comprises:
    repeating the warping, the comparing, and the updating for a plurality of iterations.

6. The method of claim 5, wherein repeating the warping, the comparing, and the updating for a plurality of iterations comprises:
    repeating the warping, the comparing, and the updating for a plurality of iterations until a difference between the warped current tissue material property distribution and the measured tissue material property distribution is less than a threshold value.

7. The method of claim 5, wherein repeating the warping, the comparing, and the updating for a plurality of iterations comprises:

repeating the warping, the comparing, and the updating for a plurality of iterations until a predetermined maximum number of iterations is reached.

8. The method of claim 5, wherein deforming the target organ in the pre-operative 3D medical image volume using the biomechanical tissue model with the patient-specific material properties with the deformation of the target organ in the pre-operative 3D medical image volume constrained by the patient-specific boundary conditions comprises:
deforming the target organ in the pre-operative 3D medical image volume using the biomechanical tissue model with the current tissue material property distribution resulting from a final iteration of the plurality of iterations with the deformation of the target organ in the pre-operative 3D medical image volume constrained by the patient-specific boundary conditions.

9. The method of claim 1, wherein the current tissue material property distribution is a tissue stiffness distribution.

10. The method of claim 1, further comprising:
performing an initial rigid alignment of the pre-operative 3D medical image volume and the intra-operative 3D B-mode ultrasound volume prior to determining the patient-specific boundary conditions, determining the patient-specific material properties, and deforming the target organ in the pre-operative 3D medical image volume using the biomechanical tissue model.

11. The method of claim 1, further comprising:
overlaying the deformed target organ in the pre-operative 3D medical image volume on at least one of the intra-operative 3D B-mode ultrasound volume or one or more intra-operative 2D B-mode ultrasound images.

12. The method of claim 1, further comprising:
deforming a map of target points defined for the target organ in the pre-operative 3D medical image volume using a non-rigid transformation corresponding to the deformation of the target organ in the pre-operative 3D medical image volume using the biomechanical tissue model; and
overlaying the deformed map of target points defined for the target organ on at least one of the intra-operative 3D B-mode ultrasound volume or one or more intra-operative 2D B-mode ultrasound images.

13. The method of claim 1, further comprising:
mapping one or more intra-operative 2D B-mode ultrasound images to a coordinate system of the pre-operative 3D medical image volume based on a non-rigid transformation corresponding to the deformation of the target organ in the pre-operative 3D medical image volume using the biomechanical tissue model.

14. The method of claim 1, wherein the pre-operative 3D medical image volume is one of a computed tomography volume or a magnetic resonance imaging volume.

15. The method of claim 1, wherein the target organ is one of a liver or a prostate.

16. An apparatus for registering a pre-operative 3D medical image volume of a target organ to intra-operative ultrasound images, comprising:
a processor; and
a memory storing computer program instructions, which when executed by the processor cause the processor to perform operations comprising:
acquiring an intra-operative 3D B-mode ultrasound volume and an intra-operative 3D ultrasound elastography volume by acquiring and interleaving a stream of 2D B-mode ultrasound images and a stream of 2D ultrasound elastography images;
determining patient-specific boundary conditions for a biomechanical tissue model of a target organ using the intra-operative 3D B-mode ultrasound volume, wherein the biomechanical tissue model is constructed on a pre-operative tissue domain defined by a segmentation of the target organ in the pre-operative 3D medical image volume, the patient-specific boundary conditions determined by:
establishing surface correspondences on a surface of the target organ segmented in the pre-operative 3D medical image volume and a surface of the target organ segmented in the intra-operative 3D B-mode ultrasound volume; and
designating boundary conditions for the biomechanical tissue model that constrain deformation of the target organ in the pre-operative 3D medical image volume based on displacements between the surface correspondences on the surface of the target organ segmented in the pre-operative 3D medical image volume and the surface of the target organ segmented in the intra-operative 3D B-mode ultrasound volume;
determining patient-specific material properties for the biomechanical tissue model of the target organ using the intra-operative 3D ultrasound elastography volume by:
warping the pre-operative tissue domain using the biomechanical tissue model based on the patient-specific boundary conditions to warp a current tissue material property distribution, the pre-operative tissue domain warped such that locations of the surface correspondences on the target organ in the pre-operative 3D medical image volume match the surface correspondences on the target organ in the intra-operative 3D B-mode ultrasound volume,
comparing the warped current tissue material property distribution with a measured tissue material property distribution measured from the intra-operative 3D ultrasound elastography volume, and
updating the current tissue material property distribution based on the comparison, wherein the patient-specific material properties include a distribution of spatially varying values of a tissue property; and
deforming the target organ in the pre-operative 3D medical image volume using the biomechanical tissue model with the patient-specific material properties, wherein the deformation of the target organ in the pre-operative 3D medical image volume is constrained by the patient-specific boundary conditions.

17. The apparatus of claim 16, wherein determining patient-specific material properties for the biomechanical tissue model of the target organ using the intra-operative 3D ultrasound elastography volume comprises:
repeating the warping, the comparing, and the updating for a plurality of iterations.

18. A non-transitory computer readable medium storing computer program instructions for registering a pre-operative 3D medical image volume of a target organ to intra-operative ultrasound images, the computer program instructions when executed by a processor cause the processor to perform operations comprising:
acquiring an intra-operative 3D B-mode ultrasound volume and an intra-operative 3D ultrasound elastography volume by acquiring and interleaving a stream of 2D B-mode ultrasound images and a stream of 2D ultrasound elastography images;
determining patient-specific boundary conditions for a biomechanical tissue model of a target organ using the intra-operative 3D B-mode ultrasound volume, wherein the biomechanical tissue model is constructed on a pre-operative tissue domain defined by a segmentation of the target organ in the pre-operative 3D medical image volume, the patient-specific boundary conditions determined by:

establishing surface correspondences on a surface of the target organ segmented in the pre-operative 3D medical image volume and a surface of the target organ segmented in the intra-operative 3D B-mode ultrasound volume; and designating boundary conditions for the biomechanical tissue model that constrain deformation of the target organ in the pre-operative 3D medical image volume based on displacements between the surface correspondences on the surface of the target organ segmented in the pre-operative 3D medical image volume and the surface of the target organ segmented in the intra-operative 3D B-mode ultrasound volume;

determining patient-specific material properties for the biomechanical tissue model of the target organ using the intra-operative 3D ultrasound elastography volume by:

warping the pre-operative tissue domain using the biomechanical tissue model based on the patient-specific boundary conditions to warp a current tissue material property distribution, the pre-operative tissue domain warped such that locations of the surface correspondences on the target organ in the pre-operative 3D medical image volume match the surface correspondences on the target organ in the intra-operative 3D B-mode ultrasound volume, comparing the warped current tissue material property distribution with a measured tissue material property distribution measured from the intra-operative 3D ultrasound elastography volume, and updating the current tissue material property distribution based on the comparison, wherein the patient-specific material properties include a distribution of spatially varying values of a tissue property; and deforming the target organ in the pre-operative 3D medical image volume using the biomechanical tissue model with the patient-specific material properties, wherein the deformation of the target organ in the pre-operative 3D medical image volume is constrained by the patient-specific boundary conditions.

19. The non-transitory computer readable medium of claim 18, wherein determining patient-specific material properties for the biomechanical tissue model of the target organ using the intra-operative 3D ultrasound elastography volume comprises:

repeating the warping, the comparing, and the updating for a plurality of iterations.

* * * * *